US010384240B2

United States Patent
Hayakawa et al.

(10) Patent No.: US 10,384,240 B2
(45) Date of Patent: Aug. 20, 2019

(54) METHOD AND APPARATUS FOR STERILIZING DRINK SUPPLY PIPELINE

(71) Applicant: Dai Nippon Printing Co., Ltd., Tokyo (JP)

(72) Inventors: Atsushi Hayakawa, Tokyo (JP); Shuta Ito, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 300 days.

(21) Appl. No.: 14/895,622

(22) PCT Filed: Jun. 24, 2014

(86) PCT No.: PCT/JP2014/066701
§ 371 (c)(1),
(2) Date: Dec. 3, 2015

(87) PCT Pub. No.: WO2014/208551
PCT Pub. Date: Dec. 31, 2014

(65) Prior Publication Data
US 2016/0121376 A1 May 5, 2016

(30) Foreign Application Priority Data
Jun. 25, 2013 (JP) .................. 2013-132409

(51) Int. Cl.
*A61L 2/07* (2006.01)
*B08B 9/032* (2006.01)
(Continued)

(52) U.S. Cl.
CPC ............ *B08B 9/0321* (2013.01); *A61L 2/04* (2013.01); *A61L 2/07* (2013.01); *B08B 3/10* (2013.01);
(Continued)

(58) Field of Classification Search
CPC ..................................... A61L 2/04; A61L 2/07
See application file for complete search history.

(56) References Cited

U.S. PATENT DOCUMENTS 4,414,036 A * 11/1983 Anderson ............... B67C 3/001
134/166 R
4,989,649 A    2/1991 Weiler et al.
(Continued)

FOREIGN PATENT DOCUMENTS

EP    0 428 009 A1    5/1991
JP    08-183595 A1    7/1996
(Continued)

OTHER PUBLICATIONS

Earle. Unit Operations in Food Processing Chapter 6: Heat Transfer Applications. 1983. (Year: 1983).*
(Continued)

*Primary Examiner* — Donald R Spamer
(74) *Attorney, Agent, or Firm* — Burr & Brown, PLLC (57) ABSTRACT

Hot water or heated steam is fed to a drink supply pipe line for simultaneously supplying drink to a plurality of filling nozzles, while exhausting the hot water or heated steam from all the filling nozzles, F-values are calculated by detecting temperatures at a plurality of predetermined portions of the drink supply pipe line and all the filling nozzles at every predetermined time interval, and a sterilizing process is ended at a time when a minimum F-value reaches an aimed value. According to such method, the sterilization to the drink supply pipe line can be smoothly performed.

11 Claims, 6 Drawing Sheets

(51) Int. Cl.
*B67C 3/00* (2006.01)
*B67C 7/00* (2006.01)
*A61L 2/04* (2006.01)
*B08B 3/10* (2006.01)
*B08B 9/027* (2006.01)

(52) U.S. Cl.
CPC ............ *B08B 9/027* (2013.01); *B08B 9/0325* (2013.01); *B67C 3/001* (2013.01); *B67C 7/0073* (2013.01); *A61L 2202/14* (2013.01); *B08B 2230/01* (2013.01); *B65B 2210/06* (2013.01); *B65B 2210/08* (2013.01)

(56) References Cited

U.S. PATENT DOCUMENTS

| | | | | |
|---|---|---|---|---|
| 5,785,864 | A | * | 7/1998 | Teran ........................ C02F 1/78 210/143 |
| 2003/0183249 | A1 | * | 10/2003 | Nissinen ............... B08B 9/0325 134/22.11 |
| 2009/0130274 | A1 | * | 5/2009 | Iwashita ............... B65B 55/025 426/394 |
| 2009/0320415 | A1 | | 12/2009 | Senbon et al. |

FOREIGN PATENT DOCUMENTS

| | | |
|---|---|---|
| JP | 09-095302 A1 | 4/1997 |
| JP | 11-281500 A1 | 10/1999 |
| JP | 2000-153245 A1 | 6/2000 |
| JP | 3176912 B2 | 6/2001 |
| JP | 2002-539893 A1 | 11/2002 |
| JP | 2007-022600 A1 | 2/2007 |
| JP | 2007-215893 A1 | 8/2007 |
| JP | 2007-331801 A1 | 12/2007 |
| JP | 4120283 B2 | 7/2008 |
| JP | 2013-042814 A1 | 3/2013 |
| WO | 2008/012996 A1 | 1/2008 |

OTHER PUBLICATIONS

J. Kao, et al., "Thermal Process Calculations for Different z and $j_c$ Values Using a Hand-Held Calculator," *Journal of Food Science*, vol. 47, No. 1, Jan. 1, 1982, pp. 193-197.

Japanese Office Action (Application No. 2015-524059) dated Apr. 24, 2018 (with English translation).

International Search Report (Application No. PCT/JP2014/066701) dated Sep. 22, 2014.

U.S. Appl. No. 14/646,552, filed May 21, 2015, Atsushi Hayakawa et al.

* cited by examiner

METHOD AND APPARATUS FOR STERILIZING DRINK SUPPLY PIPELINE

BACKGROUND OF THE INVENTION

1. Field of the Invention

The present invention relates to method and apparatus for sterilizing a pipe line of a drink supply system (hereinafter, called drink supply pipe line) for filling a container such as PET bottle with drink.

2. Description of Related Art

At a time when it is required to fill a container such as bottle with a drink from an aseptic drink filling machine, it is of course not only necessary to sterilize a drink itself so as to keep an aseptic condition, but also necessary to preliminarily clean an interior of a drink supply pipe line provided with a surge tank, a liquid feed pipe, a drink filling nozzle and so on of the aseptic drink filling machine and then to sterilize the drink supply pipe line so as to create and keep an aseptic condition.

In a known technology, an F-value as a sterilization value to the drink itself passing through the interior of a drink filling path has been measured so as to confirm whether it is worthwhile for the sterilization of the drink to receive quality guarantee or not, based on history information thereof (for example, see Patent Document 4).

In addition, for the drink supply pipe line of the aseptic drink filling machine, a CIP (Cleaning in Place) treatment and an SIP (Sterilizing in Place) treatment have been performed at every time when a kind of a drink is periodically changed (for example, see Patent Documents 1, 2 and 3).

The CIP treatment is performed, for example, by flowing a cleaning liquid prepared with water, to which alkaline chemical agent such as caustic soda is added, in a flow path from an inside of a pipe line of a drink filling path to a filling nozzle of a filling machine, and thereafter, by filling a cleaning liquid prepared with water to which acidic chemical agent is added. According to such treatment, remaining content of previously filled drink adhering to the drink filling path can be removed (see, for example, Patent Documents 1, 2, and 3).

The SIP treatment is a treatment for preliminarily sterilizing the interior of the drink supply pipe line before drink filling working, and for example, this SIP treatment is performed by circulating heated steam or hot water through the drink filling path cleaned by the CIP treatment mentioned above. According to such treatment, the interior of the drink filling path can be sterilized to thereby provide an aseptic condition (see, for example, paragraph [0003] of Patent Document 3).

PRIOR ART DOCUMENT

Patent Document

Patent Document 1: Japanese Patent Laid-open Publication No. 2007-331801
Patent Document 2: Japanese Patent Laid-open Publication No. 2000-153245
Patent Document 3: Japanese Patent Laid-open Publication No. 2007-22600
Patent Document 4: Japanese Patent Laid-open Publication No. 2007-215893

SUMMARY OF THE INVENTION

Problem to be Solved by the Invention

In a conventional technology concerning products of drink and food, sever F-value control and management have been performed because of change in quality such as taste and the like of the drink and food products themselves according to heating time (short or long heating time).

However, because a drink supply pipe line of an aseptic drink filling system is constructed mainly of metal material such as stainless steel member, in the conventional technology, the quality of a drink is hardly changed, and accordingly, F-value has been relatively roughly controlled.

For example, when a heating treatment is preformed at a temperature of 130° C. for 30 minutes, the F-value is 233, and it has been known in experience that such F-value has no problem for performing the sterilizing treatment to a drink supply pipe line. Based in such knowledge, temperatures at portions, at which the temperatures of the drink supply pipe line are difficult to be increased while heated steam or hot water being flowed in the drink supply pipe line, are measured by temperature sensors, and when the temperatures at these portions reach 130° C., a timer operates, and after elapse of 30 minutes of the timer, the heating treatment by the heated steam or like to the drink supply pipe line is ended.

Figure 7:
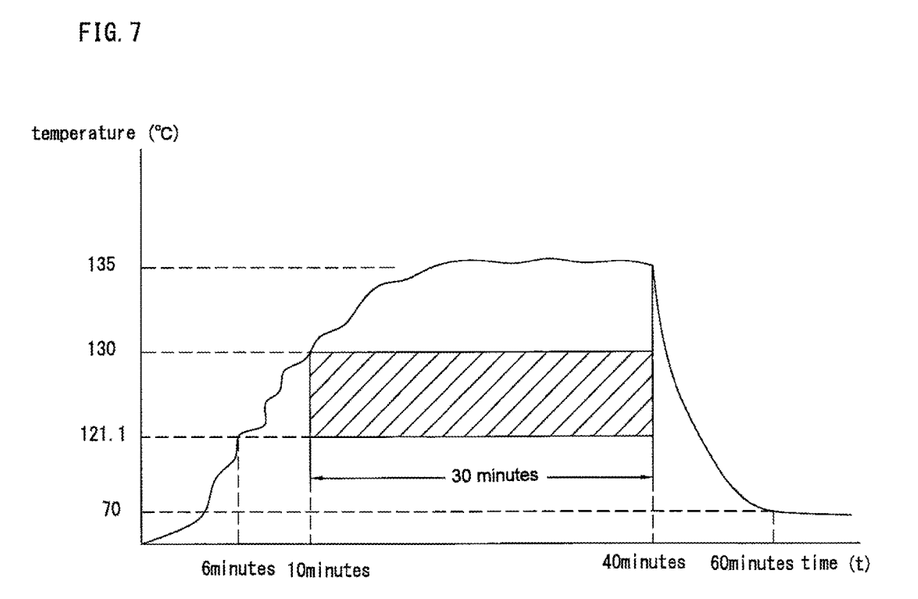
FIG. 7 is a graph representing a heating method for the drink supply pipe line with a relationship between temperature and time according to a conventional technology.

FIG. 7 is a graph representing a heating method for the drink supply pipe line using a relationship between temperature and time. That is, the drink supply pipe line starts to be heated by feeding steam or like for 30 minutes from a point time at which a lowest temperature among the temperatures measured by the temperature sensors arranged for the various portions of the drink supply pipe line, and after 30 minutes passes, the supply of the steam or like is stopped. Thereafter, instead of the steam or like, an aseptic cooling wind or like is supplied to cool the interior of the drink supply pipe line. In FIG. 7, the reason why the temperature is increased to 135° C. resides in consideration of safeness in temperature change. In FIG. 7, a condition for the sterilization resides in indication of the temperature of more than 130° C. for 30 minutes, and the hatched area (portion) corresponds to the F-value of 233. However, in actual, an integrated area (portion) of the F-value of a portion over the temperature of 130° C. is ignored.

However, in accordance with recent requirement of small energy consumption, attention has been paid to largeness of heat energy to be consumed for an SIP treatment, as well as length of time required for the SIP treatment in viewpoint of productivity of drink.

Therefore, in order to solve the problems mentioned above, an object of the present invention is to provide method and apparatus for sterilizing a drink supply pipe line.

Means for Solving the Problems

The inventors of the present invention studied and checked an F-value control and management for rethinking the heating energy and sterilizing time required for an SIP (Sterilizing in Place) treatment, and they found out that the F-value reaches the value of 233 for a time less than 30 minutes because, by controlling sterilization effect based on integration with the F-value in addition to the control of the time merely after reaching 130° C., the F-value integration from 121.1° C. to 130° C. and the F-value integration over 130° C. can be controlled.

Furthermore, in general, inside the filler, the drink supply pipe line is branched in plural numbers via a manifold, and the branched pipe line sections are connected at their terminal ends to filling nozzles. In a conventional technology, a temperature sensor is mounted to every branched pipe line section to measure the F-value. However, according to an experiment of the inventors of the present invention, it was found through experiment that temperatures detected to the respective filling nozzles of the respective branched pipe line sections are different, and therefore, in order to properly perform the SIP treatment, it is considered to be necessary to mount the temperature sensors to the filling nozzles, preferably, one temperature sensor for one filling nozzle, to measure the F-value of each of the filling nozzles.

Further, although it may be possible to control the SIP treatment by measuring the F-values of all the filling nozzles, respectively, it is considered to be possible to control the SIP treatment by measuring the temperature of the temperature sensors of the respective filling nozzles and times for passing steam, hot water or the like without measuring the F-values.

The present invention was conceived based on the above findings and is characterized by the following configurations.

It is further to be noted that although the description is made with parentheses to reference numerals in figures, the present invention is not limited thereto.

That is, the present invention according to a first aspect adopts a method of sterilizing a drink supply pipe line, wherein hot water or heated steam is fed to a drink supply pipe line (7) for simultaneously supplying drink to a plurality of filling nozzles (2a), while exhausting the hot water or heated steam from all the filling nozzles (2a), F-values are calculated by detecting temperatures at a plurality of predetermined portions of the drink supply pipe line and all the filling nozzles (2a) at every predetermined time interval, and a sterilizing process is ended at a time when a minimum F-value reaches an aimed value.

According to a second aspect of the present invention, in the method of sterilizing a drink supply pipe line according to the first aspect, it may be preferred that the drink supply pipe line (7) is provided with a heat sterilizing section (18), and the F-values are detected at the predetermined portions of the heat sterilizing section (18).

According to a third aspect of the present invention, in the method of sterilizing a drink supply pipe line according to the second aspect, it may be preferred that a return path (6) is provided for the upstream side pipe line section (7a) going through the heat sterilizing section (18) of the drink supply pipe line (7) to thereby form an upstream side circulation path, the F-values are calculated while flowing the hot water from the upstream side pipe line section (7a), and the F-values are also calculated while flowing the heated steam to the downstream side pipe line section (7b) extending from the upstream side pipe line section (7a) to the filling nozzles (2a), and the sterilizing process is ended at a time when each of the minimum F-values reaches the aimed valve.

According to a fourth aspect to the present invention, in the method of sterilizing a drink supply pipe line according to any one of the first to third aspects, it may be preferred that the F-value is calculated by using a following equation 1.

$$F = \int_{t_0}^{t_1} 10^{(T-Tr)/Z} dt \quad \text{[Equation 1]}$$

(wherein T is an optional sterilizing temperature (° C.), $$10^{(T-Tr)/Z}$$

is a fatality rate at the optional temperature T, Tr is a reference temperature (° C.), and Z is a Z value (° C.)

In a case where the temperature T is constant and heating is performed for $t_T$ minutes, the F-value is as follows.

$$F = t_T \times 10^{(T-Tr)/Z} \quad \text{[Equation 2]}$$

Further, the present invention according to a fifth aspect adopts a method of sterilizing a drink supplying pipe line, wherein hot water or heated steam is fed to a drink supply pipe line for simultaneously supplying drink to a plurality of filling nozzles, and temperatures at a plurality of predetermined portions of the drink supply pipe line and all the filling nozzles at every predetermined time interval while exhausting the hot water or heated steam through all the filling nozzles to thereby perform a sterilizing process.

According to a sixth aspect of the present invention, in the method of sterilizing a drink supply pipe line according to the fifth aspect, it may be preferred that in a case where there exists any filling nozzle of which temperature does not increase to the predetermined value within the predetermined time interval, a signal specifying that filling nozzle or a signal indicating abnormality of the sterilizing process is generated.

The present invention according to a seventh aspect adopts an apparatus for sterilizing a drink supplying pipe line, wherein a temperature sensor or a pressure sensor is provided for each of a plurality of filling nozzles (2a), a temperature sensor and a pressure sensor is also provided for a predetermined portion of a drink supplying pipe line (7) for simultaneously supplying drink to the filling nozzles (2a), hot water or heated steam is supplied to all the filling nozzles (2a), and while exhausting the hot water or heated steam from all the filling nozzles (2a), F-values are calculated by detecting temperatures at a plurality of predetermined portions of the drink supply pipe line (7) and all the filling nozzles (2a) at every predetermined time interval, and a sterilizing process is ended at a time when a minimum F-value reaches an aimed value.

According to an eighth aspect of the present invention, in the apparatus for sterilizing a drink supply pipe line according to the seventh aspect, it may be preferred that the drink supply pipe line (7) is provided with a heat sterilizing section (18) and the F-values are detected by the temperature sensors or pressure sensors provided for the predetermined portions of the heat sterilizing section (18).

According to a ninth aspect of the present invention, in the apparatus for sterilizing a drink supply pipe line according to the seventh aspect, it may be preferred that a return path (6) is provided for the upstream side pipe line section (7a) going through the heat sterilizing section (18) of the drink supply pipe line (7) to thereby form an upstream side circulation path, the F-values are calculated while flowing the hot water from the upstream side pipe line section (7a) and the F-values are also calculated while flowing the heated steam to the downstream side pipe line section (7b) extending from the upstream side pipe line section (7a) to the filling nozzles (2a), and the sterilizing process is ended at a time when each of the minimum F-values reaches the aimed valve.

Furthermore, the present invention according to a tenth aspect adopts an apparatus for sterilizing a drink supply pipe line, wherein a temperature sensor or a pressure sensor is provided for each of a plurality of filling nozzles, a temperature sensor and a pressure sensor is also provided for a predetermined portion of a drink supplying pipe line for simultaneously supplying drink to the filling nozzles, hot water or heated steam is supplied to all the filling nozzles, and while exhausting the hot water or heated steam from all the filling nozzles, F-values are calculated by detecting temperatures at a plurality of predetermined portions of the drink supply pipe line and all the filling nozzles at every predetermined time interval, and a sterilizing process is ended at a time when a minimum F-value reaches an aimed value.

Further, according to an eleventh aspect of the present invention, in the apparatus for sterilizing a drink supply pipe line according to the tenth aspect, it may be preferred that in a case where there exists any filling nozzle of which temperature does not increase to the predetermined value within the predetermined time interval, a signal specifying that filling nozzle or a signal indicating abnormality of the sterilizing process is generated.

Effects of the Invention

According to the present invention, as to the SIP treatment of the drink supply pipe line (7) of the aseptic filling system, the integration (accumulation calculation) is started in an earlier stage, and the sterilizing process is ended when the F-value reaches an aimed value. Therefore, the aseptically sterilizing treatment to the drink supply pipe line can be precisely and speedily achieved compared with a conventional technology. Accordingly, an amount of the hot water or heated steam for sterilizing the drink supply pipe line (7) can be removed, and the drink filling working can be hence started in an early stage, the production time interval at the drink changing operation can be shortened, and hence, the production efficiency can be improved.

In addition, not only the F-value as to the drink supplying pipe line (7), but also the F-values as to all the filling nozzles are calculated, and in additional consideration of these F-values, since it is judged whether the F-value reaches the aimed value or not, the sterilizing treatment to the entire arrangement of the drink supply pipe line (7) can be speedily and properly performed.

Furthermore, in the present invention, in the case where the hot water or heated steam is fed to a drink supply pipe line for simultaneously supplying the drink to a plurality of filling nozzles, and the temperatures at a plurality of predetermined portions of the drink supply pipe line and all the filling nozzles at every predetermined time interval while exhausting the hot water or heated steam through all the filling nozzles to thereby perform the sterilizing process, the aseptically sterilizing treatment to the drink supply pipe line (7) of the drink filling system can be precisely and speedily performed compared with the conventional technology by, for example, only measuring the temperature of the filling nozzle and supplying time of the heated steam or like without calculating the F-value.

DETAILED DESCRIPTION OF THE INVENTION

An embodiment of the present invention will be explained hereunder with reference to the accompanying drawings.

First Embodiment 1

Hereunder, a configuration or structure of the drink filling system is first explained, and then, method and apparatus for sterilizing the drink supply pipe line disposed inside the aseptic filling system will be explained.

Figure 1:
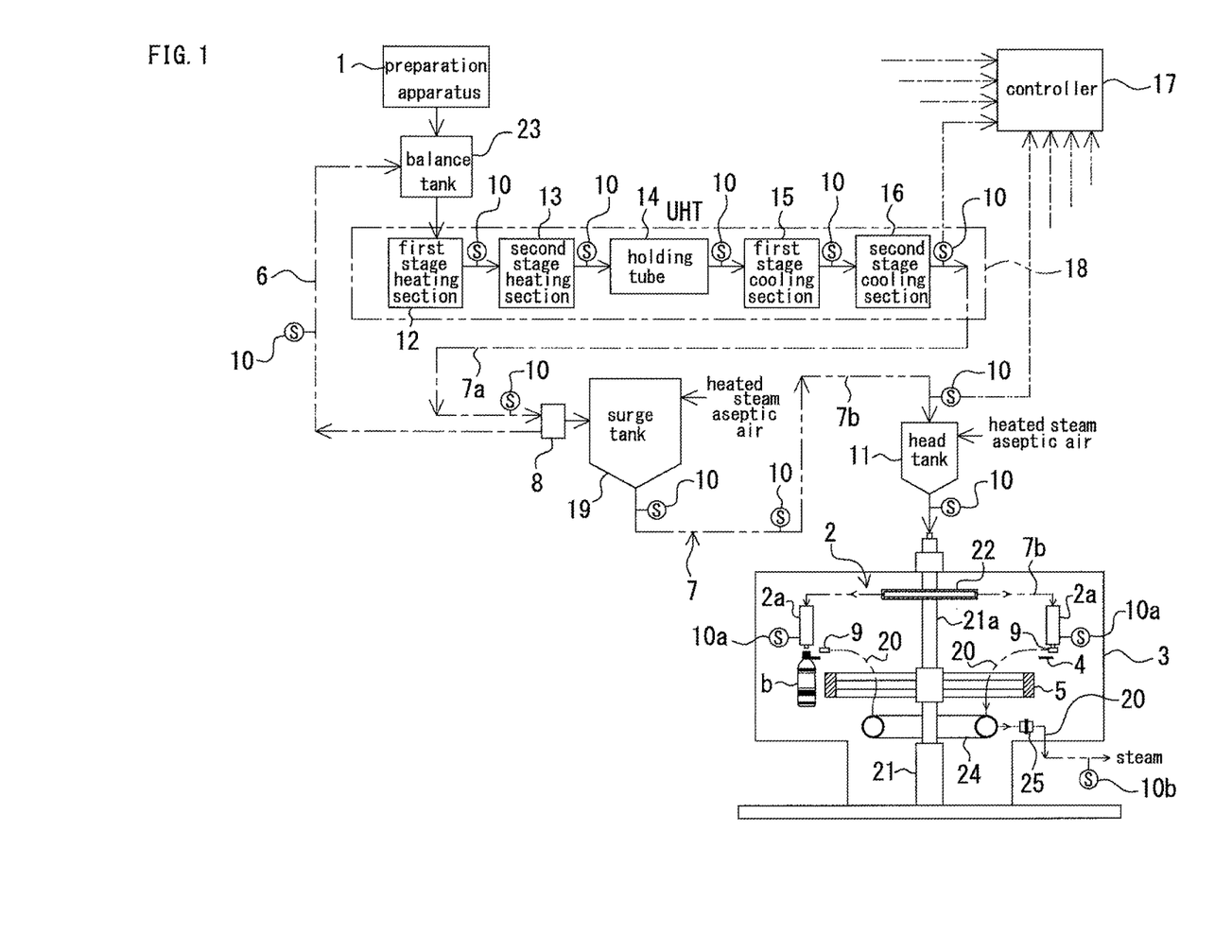
FIG. 1 is a block diagram showing a drink filling system according to the present invention.

As shown in FIG. 1, the drink filling system is provided with a drink preparation apparatus 1 and a filler 2 for filling a bottle b as a container with drink.

The preparation apparatus 1 is an apparatus for preparing, for example, tea drink, fruit drink and the like at a predetermined composition rate (blended rate), and since such preparation apparatus 1 is known one, detailed explanation thereof is omitted herein.

The preparation apparatus 1 and a filling nozzle 2a of the filler 2 are connected by means of a drink supply pipe line 7.

The aseptic filling system is also provided with a bottle conveying path for conveying the bottle b as a container, which is filled with the drink, to the filler 2 and conveying the bottle b filled with the drink to a capper, not shown. The conveying path is generally composed of a number of wheel rows and grippers 4 and so on arranged around each wheel.

Figure 2:
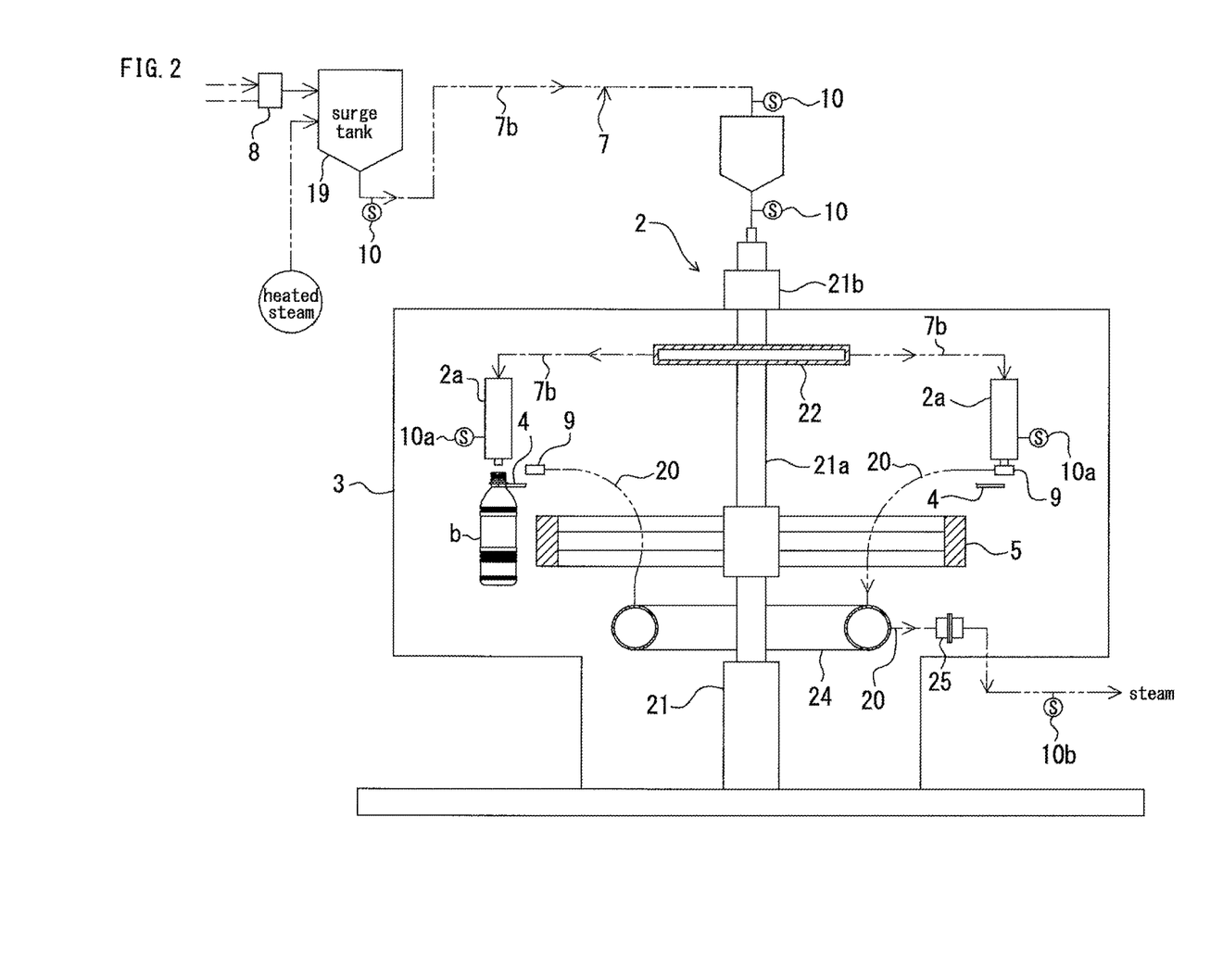
FIG. 2 is a schematic diagram of a filler in the drink filling system, in which a right half shows a condition in which an SIP treatment is performed and a left half shows a drink filling state.

The filler 2 is a filling machine for filling a number of bottles b with the drink at high speed, and as shown in FIG. 2, the filler 2 is provided with a wheel 5 constituting a part of the bottle conveying path. The wheel 5 is mounted to a portion of a turnable shaft 21a of a support shaft 21 vertically standing from a floor surface of the aseptic filling system. Around the wheel 5, the grippers 4 each gripping a neck portion of the bottle b are arranged at a constant pitch. The grippers 4 are formed to be turnable together with the wheel 5 in one direction. Furthermore, a number of filling nozzles 2a are attached around the wheel 5 at the same pitch as that of the grippers 4.

An upper portion of the support shaft 21 for stopping the turning motion is fixed to a machine frame of the filler 1, and a rotary joint 21b is disposed between the upper portion of the support shaft 21 and the turning shaft portion 21a. An upper manifold 22 is further provided to the turning shaft portion 21a at a portion below the rotary joint 21b. The support shaft 21 has a hollow portion extending from the upper portion of the support shaft 21 to the upper manifold 22, and the drink supply pipe line 7 is coupled with the upper portion of the support shat 21. A downstream side pipe line section 7b of the drink supply pipe line 7 extends to the respective filling nozzles 2a from the upper manifold 22.

When the filler 2 is driven, the wheel 5 is rotated at high speed, and the bottles b gripped by the grippers 4 are conveyed on the conveying path in synchronism with the rotating motion of the wheel 5. During this conveyance, when the bottles b are moved directly below the nozzle openings of the corresponding filling nozzles 2a, the bottles b are subsequently filled with the constant amount of the drink respectively.

The filler 2 is accommodated entirely within an aseptic chamber 3, as shown in FIG. 2, so as to fill the bottle b, which has been subjected to the sterilizing treatment, with the sterilized drink to prevent foreign substance such as bacteria from entering the bottle b. The aseptic chamber 3 is provided with an inlet port and an outlet port at its upstream side and downstream side though not shown.

As shown in FIG. 1, the drink supply pipe line 7 of the drink filling system is provided with a balance tank 23, a heat sterilizing section (UHT (Ultra High-Temperature) section) 18, a manifold valve 8, a surge tank, 19 and a head tank k 11 in this order from the upstream side toward the downstream side in view of the drink flow direction in the pipe line from the preparation apparatus 1 toward the filler 2.

The UHT section 18 is provided therein with a first stage heating section 12, a second stage heating section 13, a holding tube 14, a first stage cooling section 15, a second stage cooling section 16, and others and acts to gradually heat the drink or water supplied from the balance tank 23 while being delivered from the first stage heating section 12 to the second stage heating section 13, then heats the drink or water to an aiming temperature within the holding tube 14, and thereafter, cools the drink or water while cooling from the first stage cooling section to the second stage cooling section 16. The numbers of these heating sections and cooling sections may be changed as occasion demands.

Further, since the balance tank 23, the manifold valve 8, the surge tank 19, and the head tank 11 are all known ones, so that detailed explanations thereof are omitted herein.

Figure 3:
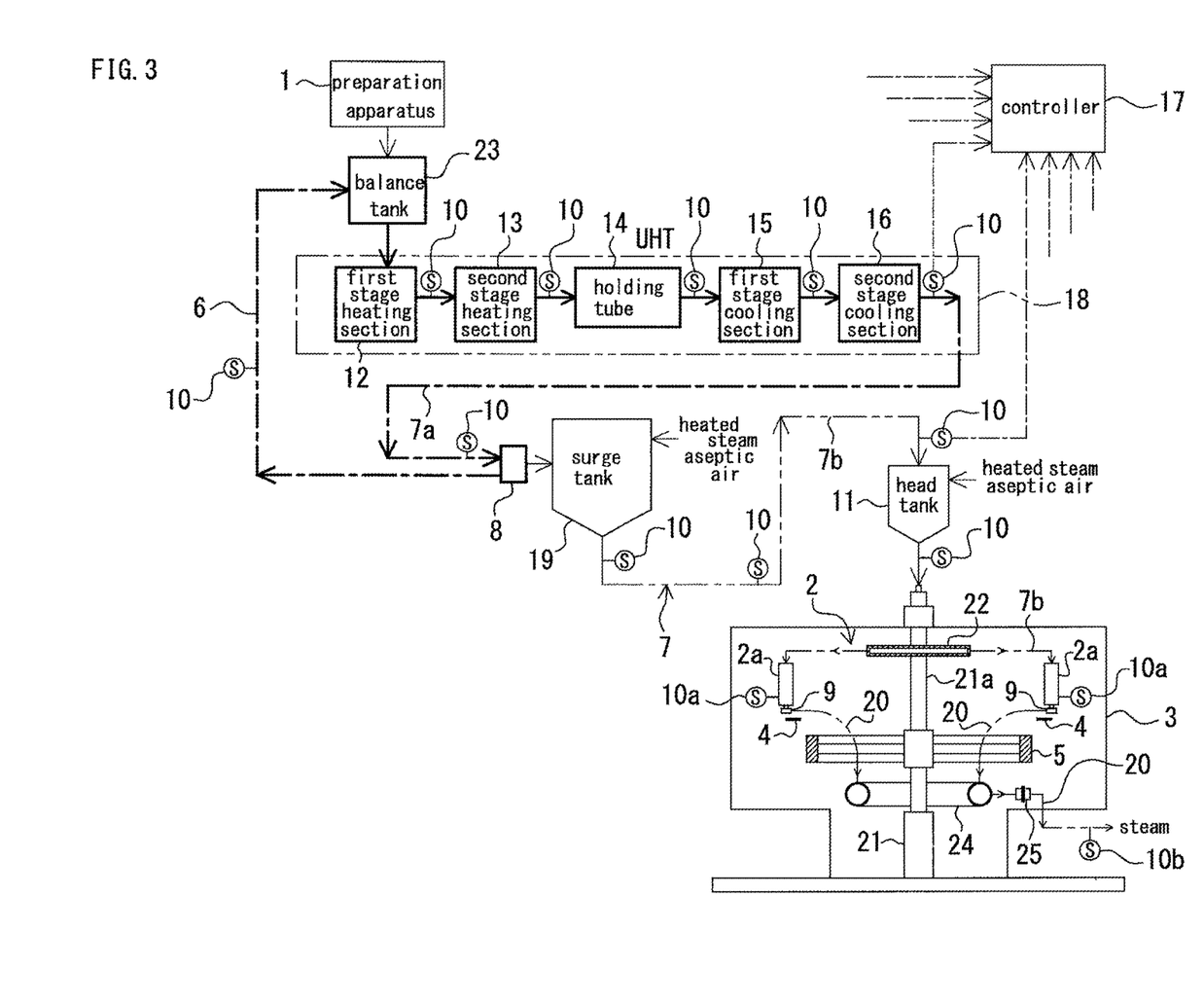
FIG. 3 is a block diagram showing a condition in which the SIP treatment is performed to a portion just before a surge tank from a heating sterilizing section using the drink supply pipe line in the drink filling system.

As shown with a thick line in FIG. 3, an upstream side pipe line section 7a of the drink supplying pipe line 7 extending to the manifold valve 8 through the balance tank 23 and the UHT section 18 is provided with a return path 6 to thereby constitute a circulation path for carrying out the SIP treatment.

Furthermore, the upstream side pipe line section 7a is provided with temperature sensors 10 at portions including a portion at which a temperature hardly increases at a time when hot water is supplied. These portions at which the temperature sensors 10 are arranged may include portions of the pipe line, for example, a portion between respective portions inside the UHT section 18, a portion just outside of the second stage cooling section 16, and a portion just before the manifold valve 8, and the temperature sensors 10 may be arranged to these portions, respectively. Informations of the temperatures measured at these portions by the respective temperature sensors 10 are sent to the controller 17.

Further, since the temperature and the pressure are under predetermined relation, a pressure sensor may be used in place of the temperature sensor 10.

Figure 4:
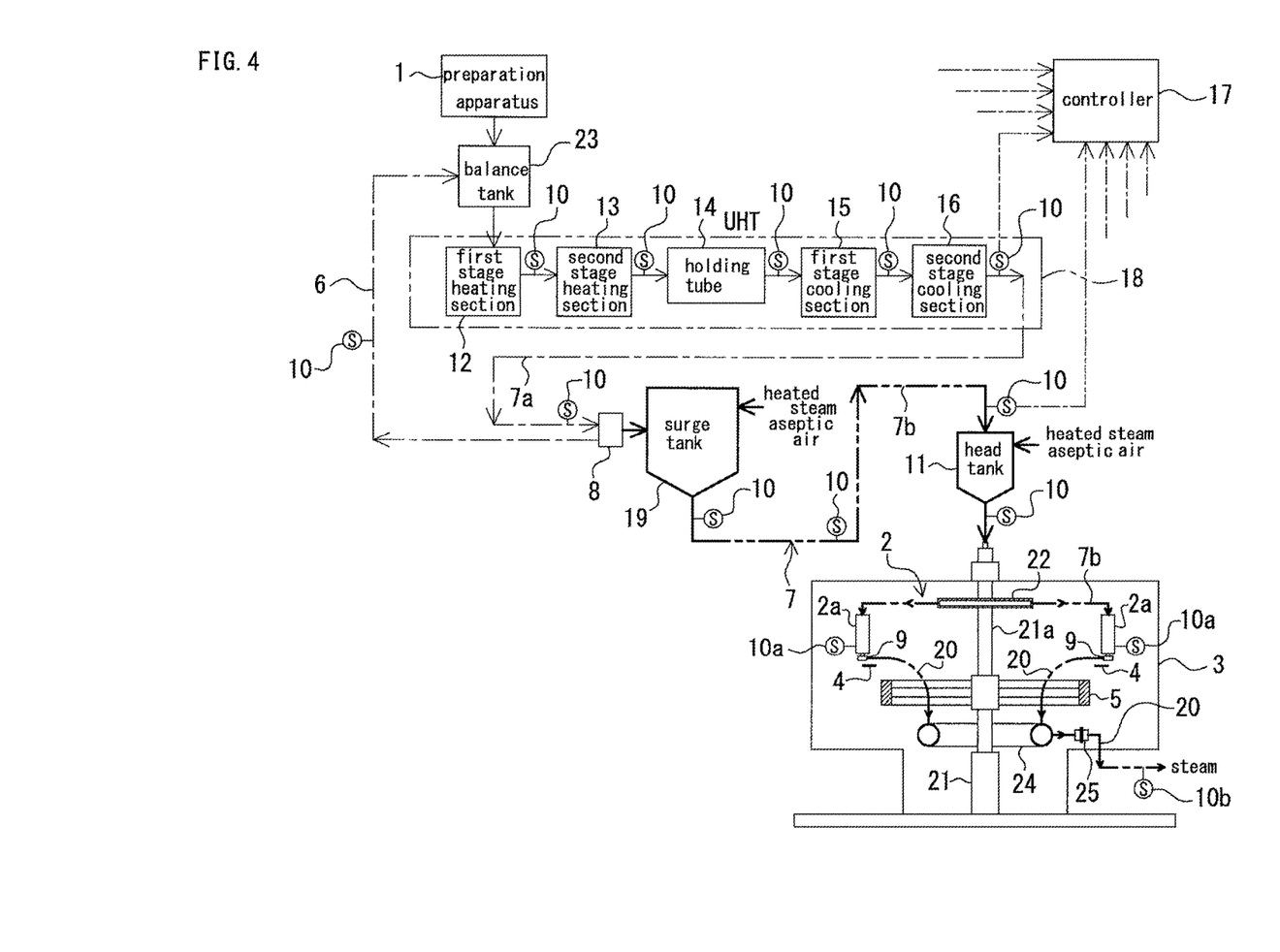
FIG. 4 is a block diagram showing a condition in which the SIP treatment is performed to a downstream side pipe line section extending from a surge tank to a filling nozzle using the drink supply pipe line of the drink filling system.

As shown with the thick line in FIG. 4, such temperature sensors 10 may be also arranged at the downstream side pipe line section 7b extending from the manifold valve 8 disposed on the downstream side than the upstream side pipe line section 7a to the filler 2 through the surge tank 19 and the head tank 11 within the drink supply pipe line 7, and arranged specifically at respective portions including a portion at which the temperature hardly increases at a time when the heated steam is supplied. These portions at which the temperature sensors 10 are arranged may include portions of the pipe line, for example, a portion near the outlet port of the surge tank 19, a bent portion on the way of the pipe line, and portions near inlet and outlet portions of the head tank 11, and the temperature sensors 10 may be arranged to these portions, respectively, on the way of the pipe line. Informations of the temperatures measured at these portions by the respective temperature sensors 10 are sent to the controller 17.

Further, the temperature may be grasped through calculation by providing a pressure sensor in place of the temperature sensor 10.

Furthermore, on the downstream side of the pipe line section 7b, cups 9 which are allowed to approach or separate from the openings of the respective filling nozzles 2a of the filler 2 for the SIP treatment. At the time when the SIP treatment is performed, the respective cups 9 are applied to the front end openings of the filling nozzles 2a of the filler 2 by the operation of the actuator, and the front end of an exhaust pipe 20 is connected to the opening of each of the filling nozzles 2a.

Further, at the time when the SIP treatment is performed, the temperature of the filling nozzle 2a increases by the flow of the hot water or heated steam from the downstream side pipe line section 7b to the filling nozzle 2a, and in order to detect such temperature of the filling nozzle 2a, a temperature sensor 10a is attached to each of the filling nozzles 2a.

Each cup 9 is coupled to a lower manifold 24 by the exhaust pipe 20. The lower manifold 24 is mounted to the turnable shaft portion 21a of the filler 2 to be integrally turnable with the wheel 5, the filling nozzle 2a and so on.

An intermittent joint 25 is provided to a portion of the exhaust pipe 20 extending outside of the aseptic chamber 3 from the lower manifold 24, and this joint 25 is connected at the time of the SIP treatment. In such case, the wheel 5, the filling nozzle 2a and the like become not turnable. When the SIP treatment is ended and the joint 25 is disconnected, the wheel 5, the filling nozzle 2a and the like become turnable.

A temperature sensor 10b may be provided to the extending portion of the exhaust pipe 20 so as to measure an F-value by this temperature sensor 10b. It is to be noted that pressure sensors may be replaced for such temperature sensors 10a and 10b to thereby obtain the temperature through calculation.

Further, to the drink supply pipe line 7, there may be further provided various types of change-over valves, and pumps, other than the manifold valve 8, the actuator, not shown, so as to be also controlled by output of the controller 17.

Hereunder, the sterilizing method for the drink filling system of the structure mentioned above will be explained with reference to FIGS. 3 to 6.

(1) When operation buttons arranged on a panel, not shown, of the controller 17 is operated, the SIP treatments are performed to the upstream side pipe line section 7a and the downstream side pipe line section 7b of the drink supply pipe line 7 in accordance with predetermined sequence (see FIGS. 3 and 4). At the time of starting the SIP treatment, the connection between the upstream side pipe line section 7a and the downstream side pipe line section 7b is shut off by controlling the operation of the manifold valve 8.

The SIP treatments for the upstream side pipe line section 7a and the downstream side pipe line section 7b may be performed in series or in parallel with each other.

(2) First, water is supplied from a water supply source, not shown, into a circulation path through the balance tank 23, and the water then circulates in the circulation path while being heated and sterilized by the UHT section 18, thereby sterilizing the interior of the upstream side pipe line section 7a.

(3) At the time when the hot water flows in the upstream side pipe line section 7a, the information of each temperature is sent to the controller 17 from each of the temperature sensors 10 arranged at plural portions of the upstream side pipe line section 7a with a predetermined constant time interval.

In the present embodiment, pH of the drink as product liquid filling the bottle b is set to be not less than 4.6, a reference temperature Tr is set to be 121.1° C. and a Z-value is set to be 10° C.

Figure 6:
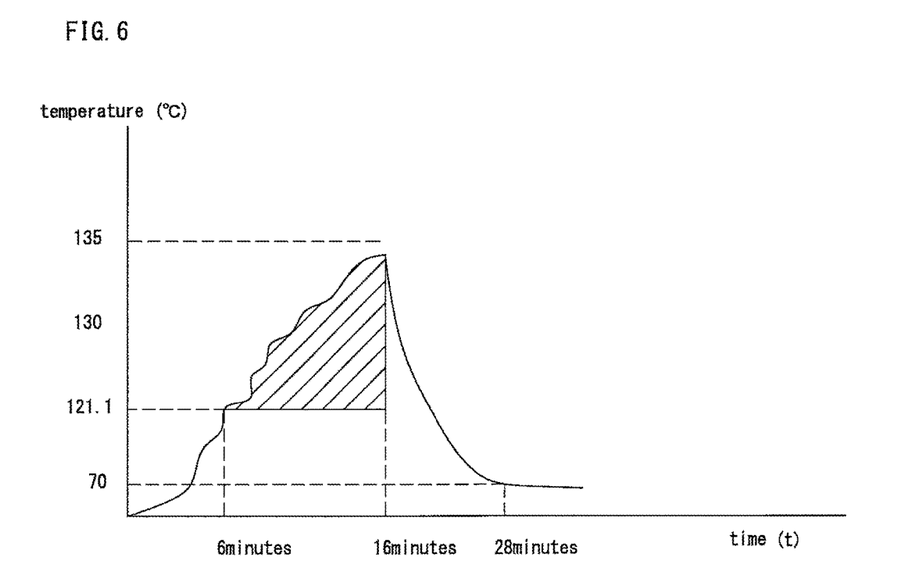
FIG. 6 is a graph representing a heating method for the drink supply pipe line with a relationship between temperature and time.

As shown in FIG. 6, at a time when the temperature at each portion increased by the heating of the hot water reaches 121.1° C., an F-value of each portion is calculated at that time point by the controller 17 with the following arithmetic equation.

$$F = \int_{t_0}^{t_1} 10^{(T-121.1)/10} \, dt \qquad \text{[Equation 3]}$$

wherein T is an optional sterilizing temperature (° C.), $$10^{(T-121.1)/10}$$

is a fatality rate at the optional temperature T, which corresponds to a heating time (minute) at the temperature of 121.1° C., in which the value 121.1 is the reference temperature (° C.), and 10 represents the Z-value (° C.).

At a time when the minimum F-value among the respective F-values calculated based on the above arithmetic equation reaches the aimed value, it is deemed that the sterilization is completed to the upstream side pipe line section 7a, the cooling water is supplied to the first stage cooling section 15 and the second stage cooling section 16 to thereby cool the hot water, and the cooled hot water then circulates continuously till the time when the next drink sterilization process starts.

The aimed value of the F-value corresponds to an area hatched in FIG. 6 concerning the temperature sensor arranged at certain portion. The hatched area in FIG. 6 corresponds to an area hatched in FIG. 7.

In a conventional technology, as shown in FIG. 7, a timer for detecting the fact of completion of the sterilization is operated at a time when all the temperature sensors indicate 130° C., and this fact is announced after 30 minutes later from the completion of sterilization. Moreover, before the temperature reaches 130° C., about 10 minutes have passed from the starting time of supplying the hot water or heated steam. On the contrary, with the present invention, the arithmetic calculation of the respective F-values is started at the time when the temperatures of all the sensors 10 reach 121.1° C., so that the time before the start of the calculation can be shortened by 6 minutes. In addition, in the conventional technology, the heating sterilization is constantly performed for about 30 minutes from the arithmetic calculation starting time while feeding the hot water or heated steam, which results in the heat accumulation to the drink supply pipe line 7 and so on, and accordingly, about 20 minutes are required for the cooling. However, according to the present invention, cumulative calculation of the F-value is started after 6 minutes from the heating start time, which is shorter by 10 minutes, in the heating time, and less heat accumulation is applied to the drink supply pipe line 7 and so on, so that the time required for the cooling can be shorten by 12 minutes. Therefore, the time interval from the heating to the cooling can be remarkably shorten to 28 minutes compared with a conventional case in which 60 minutes is required for the cooling.

Further, in the above-mentioned arithmetic equation for the F-value, the reference temperature Tr and the Z-value may be changed in accordance with kinds of drinks as product liquids.

For example, when the pH of the product drink is less than 4 to 4.6, the reference temperature Tr and the Z-value may be set to Tr=85° C. and Z-value=7.8° C., and on the other hand, when the pH of the product drink is less than 4, the reference temperature Tr and the Z-value may be set to Tr=60° C. and Z-value=5° C.

Furthermore, values to be plugged in for the above arithmetic equation in conformity with bacteria growing characteristics, circulation temperature and the like of the product liquid such as green tea, mineral water, child drink or the like may also be optionally changed.

(4) Thereafter, the drink is delivered to the balance tank 23 from the preparation apparatus 1 and then subjected to the sterilization treatment. At a timing when the water is replaced with the drink, a portion in the pipe line between the upstream side pipe line section 7a and the return circulation path is shut off, and the sterilized drink is stored in the surge tank 19.

(5) At the same time or in advance of the starting of the SIP treatment for the upstream side pipe line section 7a, the SIP treatment starts to be performed to the downstream side pipe line section 7b inclusive of the surge tank 19.

First, as shown on right half in FIG. 2 and FIG. 4, the cups 9 are applied to the openings of the filling nozzles 2a, respectively, and the exhaust pipe 20 are connected to the filling nozzles 2a, respectively, and thereafter, the heated steam is supplied into the surge tank 19 and the head tank 11 from the heated steam supply source, not shown.

This heated steam flows from the surge tank 19 into the downstream side pipe line section 7b, and after the heating of the respective sections or the like, the heated steam is discharged outside the filler 2 through the exhaust pipe 20.

(6) When the heated steam flows inside the downstream side pipe line section 7b, the temperature informations from the respective temperature sensors 10 arranged at various portions are sent to the controller with constant interval.

Furthermore, temperature informations from the temperature sensors 10a provided for the filling nozzles 2a and the temperature sensors 10b provided for the exhaust pipe 20 are also sent to the controller 17 with the constant time interval.

As shown in FIG. 6, the temperatures at the various portions increased by the heating of the heated steam reach 121.1° C., the F-values of these portions are arithmetically calculated, at this timing, based on the above-mentioned arithmetic equation by the controller 17.

At the time when the minimum F-value among the calculated respective F-values reaches the aimed value, the supply of the heated steam into the surge tank 19 and the downstream side pipe line section 7b is stopped. This aimed value of the F-value corresponds to the area hatched in FIG. 6. As can be seen from comparison result of the cases shown in FIG. 6 and FIG. 7, the time required for the SIP treatment in the downstream side pipe line section 7b can be remarkably shortened in comparison with the time for the conventional SIP treatment.

Further, in this case, in the above-mentioned arithmetic equation for the F-value, the reference temperature Tr and the Z-value may be changed in accordance with kinds of drinks as product liquids.

(7) Thereafter, the aseptic air is supplied into the downstream side pipe line section 7b, and the interior of the downstream side pipe line section 7b is then cooled to a temperature, for example, of room temperature. Thereafter, the exhaust pipe 20 is shut off, and the cups 9 are removed from the openings of the filling nozzles 2a, respectively, by an actuator, not shown.

(8) The drink is stored into the surge tank 19 from the UHT section 18 through the upstream side pipe line section 7a after the completion of the SIP treatment for the downstream side pipe line section 7b, and the drink filling operation for filling the bottles b then starts through the downstream side pipe line section 7b.

Figure 5:
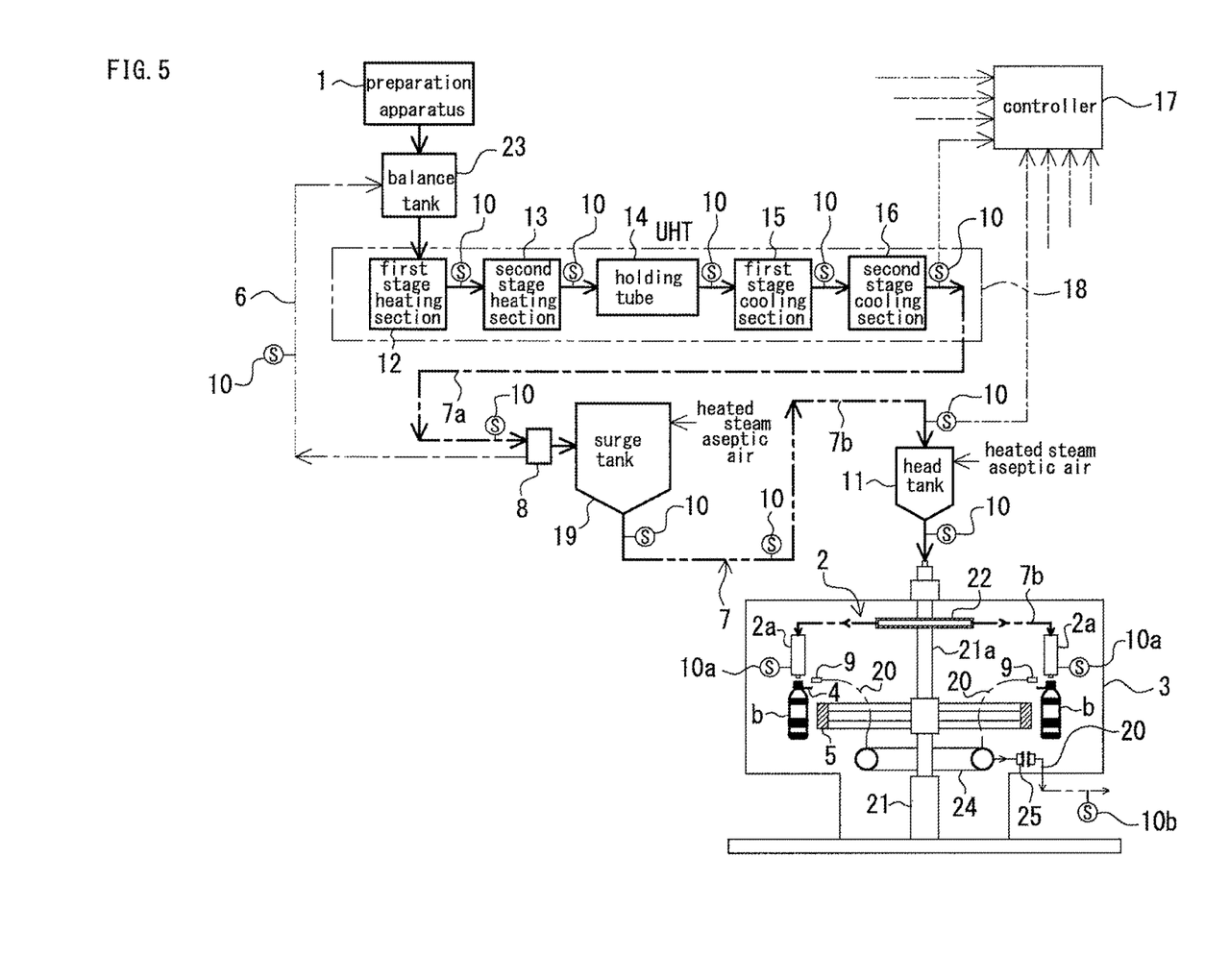
FIG. 5 is a block diagram showing a condition in which bottled drink products are produced.

As shown with the thick line in FIG. 5, the drink prepared in the drink preparation apparatus 1 is delivered into the filler 2 through the upstream side pipe line section 7a and the downstream side pipe line section 7b of the sterilized drink supply pipe line 7, and thereafter, the bottle b as a container is filled up with the drink through each of the filling nozzles 2a of the filler 2. The bottles b filled up with the drink are capped by a capper, not shown, and then fed out of the filler 2.

Embodiment 2

In this second embodiment 2, the controller 17 is provided with a calculating section, in place of the calculation section for arithmetically calculating and then outputting the above-mentioned F-value, for processing the information concerning the temperatures sent from the various sensors 10, 10a, 10b and information concerning the time for sending the hot water or heated steam to the drink supply pipe line 7 and then generating an alarm.

In this second embodiment 2, pressure sensors may be provided in place of the temperature sensors 10, 10a, 10b to grasp the temperature from the pressure sensors through the arithmetic calculation.

In the calculating section, the following explanation may be made with reference to the example shown in FIG. 6, that is, there may be installed a program for monitoring: a case where the temperatures of the filling nozzles do not reaches 121.1 even to any one of the filling nozzles after the elapse of 6 minutes from the sterilization starting time; a case where the temperatures of the filling nozzles do not reaches 130° C. at the sterilization ended time after the elapse of 16 minutes from the sterilization starting time; or both the above cases, and informing that abnormal condition is caused in the sterilization process in either one of the above cases.

The hot water or heated steam is fed to the drink supply pipe line for feeding the drink simultaneously to a plurality of the filling nozzles, and the SIP treatment is performed while discharging such hot water or heated steam from all the filling nozzles and measuring the temperature of all the filling nozzles at the predetermined portions of the drink supplying pipe line. During such SIP treatment, when the temperatures of all the temperature measuring portions increase to the predetermined values within the predetermined time period, an alarm for informing that the SIP treatment is ended is generated from the controller 17, and on the contrary, in a case where the temperature of any one of the filling nozzles does not increase to the predetermined temperature within the predetermined time period, the controller generates an alarm such that an abnormal condition is caused to such filling nozzle, or generates an alarm such that the SIP treatment is not normally performed.

When an operator recognizes the alarm of completion of the SIP treatment, the operator performs operation for stopping the SIP treatment, and on the other hand, when the operator recognizes the alarm of generation of the abnormality, the operator specifies the portion to which the sterilization was performed insufficiently, and then, for example, adjusts a valve opening degree, exchanges the valve, and removes foreign substance to thereby make proper the flow rate or amount of the hot water or heated steam.

Hereunder, the sterilization method of the drink supplying pipe line according to the second embodiment will be explained.

It is further to be noted that the second embodiment differs from the first embodiment only in the structure of the controller 17, and the difference will be explained with reference to FIGS. 3 to 6.

(1) When an operation button on a panel, not shown, of the controller 17 is operated, the SIP treatment is performed to the upstream side pipe line section 7a and the downstream side pipe line section 7b of the drink supply pipe line 7 in accordance with the predetermined procedures, respectively (refer to FIGS. 3 and 4). At the time of starting the SIP treatment, the upstream side pipe line section 7a and the downstream side pipe line section 7b are shut off from each other by the manifold 8.

The SIP treatments to the upstream side pipe line section 7a and the downstream side pipe line section 7b may be performed sequentially or in parallel to each other.

(2) Next, water is send from a water supply source, not shown, to the circulation path including the upstream side pipe line section 7a and the return path 6, and the water is then heated by the UHT 18 and circulates while being sterilized. According to such procedure, the interior of the upstream side pipe line section 7a is sterilized.

(3) At the time when the hot water flows in the upstream side pipe line section 7a, the temperature informations from the temperature sensors 10 provided at the predetermined portions of the upstream side pipe line section 7a are sent to the controller 17 with a predetermined time interval, and the hot water supply time is measured in the controller 17.

When all the temperature sensors 10 reach the predetermined temperature within the predetermined time interval, the sterilization to the upstream side pipe line section 7a is ended, and the cooling water is supplied to the first stage cooling section 15 and the second stage cooling section 16 to cool the hot water, which circulates in a waiting state for the next drink sterilization starting time.

Further, in a case if any one of the temperature sensors 10 does not increase the predetermined temperature within the predetermined time interval, an alarm such that some abnormality is caused to the portion, to which that temperature sensor 10 is provided, is generated from the controller 17.

When the operator recognizes such alarm informing of the generation of the abnormality, the operator specifies the portion to which the sterilization has not been performed sufficiently, and tries to make proper the flow rate or amount of the hot water or heated steam by, for example, adjusting the opening degree of the valve.

(4) Thereafter, the drink is fed to the balance tank 23 from the preparation apparatus 1 to start the sterilization of the drink. At the moment when the water is replaced with the drink, the connection between the upstream side pipe line section 7a and the return path 6 is shut off, and the sterilized drink is then stored in the surge tank 19.

(5) At the same time or in advance of the time when the SIP treatment to the upstream side pipe line section 7a is performed, the SIP treatment to the downstream side pipe line section is performed together with the surge tank 19.

Specifically, with reference to right half of FIG. 2 and FIG. 4, the cup 9 is first applied to a nozzles opening of each filling nozzle 2a, and after the connection of the filling nozzle 2a to the exhaust pipe 20, the heated steam is fed from the heated steam supply source, not shown, within the surge tank 19 and the head tank 11.

This heated steam flows from the surge tank 19 to the filling nozzle 2a through the downstream side pipe line section 7b to heat the various portions, and thereafter, is discharged outside the filler 2 through the exhaust pipe 20.

(6) At the time when the heated steam flows inside the downstream side pipe line section 7b, the temperature informations from the temperature sensors 10 provided at the predetermined portions of the downstream side pipe line section 7b are sent to the controller 17 with a predetermined time interval.

Further, the temperature informations from the temperature sensors 10a provided to the respective filling nozzles 2a and the temperature sensors 10b provided to the exhaust pipe 20 are also sent to the controller 17 with a predetermined time interval.

When all the temperature sensors 10, 10a, 10b reach the predetermined temperature within the predetermined time interval, the sterilization to the downstream side pipe line section 7b is ended, and the heated steam supply to the surge tank 19 and the interior of the downstream side pipe line section 7b is stopped.

Further, in a case if any of the temperature sensors 10, 10a, 10b does not increase the predetermined temperature within the predetermined time interval, an alarm such that some abnormality is caused to the portion, to which that temperature sensor 10, 10a, 10b is provided, is generated from the controller 17.

When the operator recognizes such alarm informing of the generation of the abnormality, the operator specifies the portion to which the sterilization has not been sufficiently performed, and tries to make proper the flow rate or amount of the hot water or heated steam by, for example, adjusting the opening degree of the valve, exchanging the valve or removing the foreign substance.

(7) Thereafter, the aseptic air is fed into the downstream side pipe line section 7b to thereby cool the interior thereof to a normal temperature, for example, and then, the exhaust pipe is shut off. Then, the cup 9 is removed from the nozzle opening of each filling nozzle 2a by an actuator, not shown, and the joint 25 is also disconnected.

(8) After the completion of the SIP treatment of the downstream side pipe line section 7b, the drink is stored in the surge tank 19 from the heat sterilizing section 18 through the upstream side pipe line section 7a, and the drink is then fed to the downstream side pipe line section 7b so as to start the drink filling working for filling the bottle b.

In FIG. 5, as shown with thick line, the drink prepared by the preparation apparatus 1 is fed to the filler 2 via the upstream side pipe line section 7a and the downstream side pipe line section 7b, and fills the bottle b as the container from the filling nozzle 2a of the filler 2. The bottle b filled up with the drink is capped by the capper, not shown, and is then fed out of the filler 2.

It is to be noted that although the present invention is constructed as explained hereinabove, the present invention is not limited to the embodiments described above, and many other changes and modifications may be made within the scopes of the present invention. For example, in the above-described embodiment, although the SIP treatment for the upstream side pipe line section and the SIP treatment for the downstream side pipe line section are performed by using different fluids such as hot water and heated steam, both the SIP treatments may be performed with the same kind of fluid. Furthermore, it may be possible to perform the SIP treatment by releasing the manifold valve so as to establish the communication between the upstream side pipe line section and the downstream side pipe line section to thereby flow the fluid from the upstream side pipe line section to the downstream side pipe line section. Still furthermore, the time interval for the measurement and accumulation of the F-value may be set to one-second interval other than one-minute interval, and such time interval may be changed in accordance with ability or like of a measuring equipment to be used.

REFERENCE NUMERAL

2 - - - filler
2a - - - filling nozzle
6 - - - return path
7 - - - drink supply pipe line
7a - - - upstream side pipe line section
7b - - - downstream side pipe line section
18 - - - heat sterilizing section

The invention claimed is:

1. A method of sterilizing a drink supply pipe line, the drink supply pipe line is provided a balance tank, a heat sterilizing section, a manifold valve, a surge tank and a head tank in that order from a preparation apparatus toward a filler, the heat sterilizing section comprising at first and second heating stage sections, at least first and second cooling stage sections and a holding tube interposed between the at least first and second heating stage sections and the at least first and second cooling stage sections, with a pipe fluidly connecting the at least second cooling stage section to the balance tank via the manifold valve, each of which being upstream of the surge tank, which is fluidly connected to the drink supply pipe line, such that the pipe and the manifold valve constitute a return circulation path between the at least second cooling stage section and the balance tank that is fluidly connected to the at least first heating stage section, wherein hot water or heated steam is heated by the at least first and second heating stage sections and the holding tube to an aimed temperature as the hot water or heated steam is circulated in the return circulation path upstream of the surge tank, wherein the hot water or heated steam is fed to the drink supply pipe line for simultaneously supplying drink to a plurality of filling nozzles within an aseptic chamber, while exhausting the hot water or heated steam from all the filling nozzles, F-values are calculated by detecting temperatures at a plurality of predetermined portions of the drink supply pipe line and all the filling nozzles at every predetermined time interval, and a sterilizing process is ended at a time when a minimum F-value, of all calculated F-values at the plurality of predetermined portions of the drink supply pipe line and all the filling nozzles, reaches an aimed value.

2. The method of sterilizing a drink supply pipe line according to claim 1, wherein the F-values are detected at the predetermined portions of the heat sterilizing section.

3. The method of sterilizing a drink supply pipe line according to claim 2, wherein the F-value is calculated by using a following equation 1, $$F = \int_{t_0}^{t_1} 10^{(T-Tr)/Z} dt \quad \text{[Equation 1]}$$

(wherein T is an optional sterilizing temperature (° C.), $10^{(T-Tr)/Z}$ is a fatality rate at the optional temperature T, Tr is a reference temperature (° C.), and Z is a Z value (° C.)).

4. The method of sterilizing a drink supply pipe line according to claim 2, wherein a portion of the return circulation path is provided as an upstream side pipe line section that feeds the hot water or heated steam from the heat sterilizing section to the drink supply pipe line to thereby form an upstream side path, the F-values are calculated while flowing the hot water or heated steam from the upstream side pipe line section and the F-values are also calculated while flowing the hot water or heated steam to a downstream side pipe line section extending from the upstream side pipe line section to the filling nozzles within the aseptic chamber, and the sterilizing process is ended at the time when each of the minimum F-values reaches the aimed value.

5. The method of sterilizing a drink supply pipe line according to claim 4, wherein the F-value is calculated by using a following equation 1, $$F = \int_{t_0}^{t_1} 10^{(T-Tr)/Z} dt \quad \text{[Equation 1]}$$

(wherein T is an optional sterilizing temperature (° C.), $10^{(T-Tr)/Z}$ is a fatality rate at the optional temperature T, Tr is a reference temperature (° C.), and Z is a Z value (° C.)).

6. The method of sterilizing a drink supply pipe line according to claim 1, wherein the F-value is calculated by using a following equation 1, $$F = \int_{t_0}^{t_1} 10^{(T-Tr)/Z} dt \quad \text{[Equation 1]}$$

(wherein T is an optional sterilizing temperature (° C.), $10^{(T-Tr)/Z}$ is a fatality rate at the optional temperature T, Tr is a reference temperature (° C.), and Z is a Z value (° C.)).

7. The method of sterilizing a drink supply pipe line according to claim 1, wherein in a case where there exists any filling nozzle of which temperature does not increase to a predetermined value within a predetermined time interval, a signal specifying that filling nozzle or a signal indicating abnormality of the sterilizing process is generated.

8. An apparatus for sterilizing a drink supply pipe line, the drink supply pipe line is provided a balance tank, a heat sterilizing section, a manifold valve, a surge tank and a head tank in that order from a preparation apparatus toward a filler, the heat sterilizing section comprising at least first and second heating stage sections, at least first and second cooling stage sections and a holding tube interposed between the at least first and second heating stage sections and the at least first and second cooling stage sections, with a pipe fluidly connecting the at least second cooling stage section to the balance tank via the manifold valve, each of which being upstream of the surge tank, which is fluidly connected to the drink supply pipe line, such that the pipe and the manifold valve constitute a return circulation path between the at least second cooling stage section and the balance tank that is fluidly connected to the at least first heating stage section, wherein hot water or heated steam is heated by the at least first and second heating stage sections and the holding tube to an aimed temperature as the hot water or heated steam is circulated in the return circulation path upstream of the surge tank, wherein a temperature sensor or a pressure sensor is provided for each of a plurality of filling nozzles within an aseptic chamber, a temperature sensor and a pressure sensor is also provided for a predetermined portion of the drink supply pipe line for simultaneously supplying drink to the filling nozzles, the hot water or heated steam is supplied to all the filling nozzles, and while exhausting the hot water or heated steam from all the filling nozzles, F-values are calculated by detecting temperatures at a plurality of predetermined portions of the drink supply pipe line and all the filling nozzles at every predetermined time interval, and a sterilizing process is ended at a time when a minimum F-value, of all calculated F-values at the plurality of predetermined portions of the drink supply pipe line and all the filling nozzles, reaches an aimed value.

9. The apparatus for sterilizing a drink supply pipe line according to claim 8, wherein the F-values are detected by the temperature sensors or pressure sensors provided for predetermined portions of the heat sterilizing section.

10. The apparatus for sterilizing a drink supply pipe line according to claim 9, wherein a portion of the return circulation path is provided as an upstream side pipe line section that feeds the hot water or heated steam from the heat sterilizing section to the drink supply pipe line to thereby form an upstream side path, the F-values are calculated while flowing the hot water or heated steam from the upstream side pipe line section and the F-values are also calculated while flowing the hot water or heated steam to a downstream side pipe line section extending from the upstream side pipe line section to the filling nozzles within the aseptic chamber, and the sterilizing process is ended at the time when each of the minimum F-values reaches the aimed value.

11. The apparatus for sterilizing a drink supply pipe line according to claim 8, wherein in a case where there exists any filling nozzle of which temperature does not increase to a predetermined value within a predetermined time interval, a signal specifying that filling nozzle or a signal indicating abnormality of the sterilizing process is generated.

* * * * *